(12) United States Patent
Velasco Diez et al.

(10) Patent No.: US 8,632,825 B2
(45) Date of Patent: Jan. 21, 2014

(54) ANTI-TUMOURAL EFFECTS OF CANNABINOID COMBINATIONS

(75) Inventors: Guillermo Velasco Diez, Madrid (ES); Manuel Guzman Pastor, Madrid (ES); Mar Lorente, Madrid (ES); Sofia Torres, Madrid (ES); Fatima Rodriguez, Madrid (ES)

(73) Assignees: GW Pharma Limited, Salisbury (GB); Otsuka Pharmaceutical Co., Limited, Tokyo (JP)

( * ) Notice: Subject to any disclaimer, the term of this patent is extended or adjusted under 35 U.S.C. 154(b) by 0 days.

(21) Appl. No.: 12/996,124

(22) PCT Filed: Jun. 4, 2009

(86) PCT No.: PCT/GB2009/050621
§ 371 (c)(1),
(2), (4) Date: Jan. 28, 2011

(87) PCT Pub. No.: WO2009/147439
PCT Pub. Date: Dec. 10, 2009

(65) Prior Publication Data
US 2011/0117216 A1    May 19, 2011

(30) Foreign Application Priority Data
Jun. 4, 2008  (GB) .................................. 0810195.8

(51) Int. Cl.
*A01N 65/00* (2009.01)
(52) U.S. Cl.
USPC .......................................................... 424/725
(58) Field of Classification Search
None
See application file for complete search history.

(56) References Cited

U.S. PATENT DOCUMENTS

| | | | |
|---|---|---|---|
| 6,946,150 B2 | 9/2005 | Whittle | |
| 7,968,594 B2 | 6/2011 | Guy et al. | |
| 2002/0137064 A1 | 9/2002 | Desprez et al. | |
| 2003/0021752 A1 | 1/2003 | Whittle et al. | |
| 2003/0158191 A1 | 8/2003 | Travis | |
| 2004/0039048 A1 | 2/2004 | Guzman Pastor et al. | |
| 2004/0138293 A1 | 7/2004 | Werner et al. | |
| 2005/0165259 A1 | 7/2005 | Martin | |
| 2006/0234273 A1 | 10/2006 | Desprez et al. | |
| 2006/0247304 A1 | 11/2006 | Guy et al. | |
| 2007/0072938 A1 | 3/2007 | Rose | |
| 2008/0057117 A1 | 3/2008 | Werner et al. | |
| 2008/0262099 A1 | 10/2008 | Whittle et al. | |
| 2010/0204312 A1 | 8/2010 | McAllister et al. | |
| 2011/0086113 A1 | 4/2011 | Velasco Diez et al. | |
| 2012/0225136 A1 | 9/2012 | Whittle et al. | |

FOREIGN PATENT DOCUMENTS

| | | |
|---|---|---|
| CN | 1976690 A | 6/2007 |
| EP | 1177790 A1 | 2/2002 |
| EP | 1802274 B1 | 9/2008 |
| GB | 2380129 A | 4/2003 |
| GB | 2386322 A | 9/2003 |
| GB | 2418612 A | 4/2006 |
| GB | 2448535 A | 10/2008 |
| GB | 2471987 A | 1/2011 |
| WO | WO 01/58445 A1 | 8/2001 |
| WO | WO 01/87295 A | 11/2001 |
| WO | WO-02/069993 A1 | 9/2002 |
| WO | WO 2004/041269 A2 | 5/2004 |
| WO | WO 2005/120478 A1 | 12/2005 |
| WO | WO-2006/107903 A2 | 10/2006 |
| WO | WO-2008/144475 A1 | 11/2008 |

OTHER PUBLICATIONS

Jacobsson et al., Serum-dependent effects of tamoxifen and cannabinoids upon C6 glioma cell viability. Biochem Pharmacol. Dec. 15, 2000;60(12):1807-13.
Ligresti et al., Antitumor activity of plant cannabinoids with emphasis on the effect of cannabidiol on human breast carcinoma. J Pharmacol Exp Ther. Sep. 2006;318(3):1375-87. Epub May 25, 2006.
Massi et al., Antitumor effects of cannabidiol, a nonpsychoactive cannabinoid, on human glioma cell lines. J Pharmacol Exp Ther. Mar. 2004;308(3):838-45. Epub Nov. 14, 2003.
Russo et al., A tale of two cannabinoids: the therapeutic rationale for combining tetrahydrocannabinol and cannabidiol. Med Hypotheses. 2006;66(2):234-46. Epub Oct. 4, 2005.
Vaccani et al., Cannabidiol inhibits human glioma cell migration through a cannabinoid receptor-independent mechanism. Br J Pharmacol. Apr. 2005;144(8):1032-6.
Velasco et al., Cannabinoids and gliomas. Mol Neurobiol. Aug. 2007;36(1):60-7. Epub Jun. 28, 2007.
Declaration of Sean D. McAllister and Pierre-Yves Desprez dated Nov. 26, 2012, filed in U.S. Appl. No. 12/600,553.
Exhibit A to McAllister and Desprez Declaration. Molecular Mechanisms of Cannabinoid Antitumor Activity. Grant Proposal. Forbes Norris/MDA ALS Research Center. Award notice date Apr. 5, 2005. 15 pages.
Exhibit B to McAllister and Desprez Declaration. Excel data reporting results of experiments. Nov. 26, 2012.
Exhibit C to McAllister and Desprez Declaration. Soroceanu et al., The role of ID-1 in modulating brain tumor invasion and dispersal. Neuro-Oncology. 2009;11:564. Abstract #3.
Adalpe et al., Models of malignant glioma. Drug Discovery Today: Disease Models. 2006;3(2):191-6.
Ben-Shabat et al., New cannabidiol derivatives: synthesis, binding to cannabinoid receptor, and evaluation of their antiinflammatory activity. J Med Chem. Feb. 9, 2006;49(3):1113-7.
Blazquez, C. et al., "Inhibition of tumor angiogenesis by cannabinoids," *FASEB J*. 2003; 17:529-531.
Blow, Cell migration: our protruding knowledge. Nat Meth. 2007;4:589-94.

(Continued)

*Primary Examiner* — Michael Meller
(74) *Attorney, Agent, or Firm* — Wolf, Greenfield & Sacks, P.C.

(57) ABSTRACT

The invention relates to the use of a combination of cannabinoids, particularly tetrahydrocannabinol (THC) and cannabidiol (CBD), in the manufacture of a medicament for use in the treatment of cancer. In particular the cancer to be treated is a brain tumor, more particularly a glioma, more particularly still a glioblastoma multiforme (GBM).

3 Claims, 3 Drawing Sheets

(56) References Cited

OTHER PUBLICATIONS

Boyden, The chemotactic effect of mixtures of antibody and antigen on polymorphonuclear leucocytes. J Exp Med. Mar. 1, 1962;115:453-66.

Casanova, M.L. et al., "Inhibition of skin tumor growth and angiogenesis in vivo by activation of cannabinoid receptors," *J. Clinical Investigation* Jan. 1, 2003; 111(1): 43-50.

Galve-Roperh I. et al., "Anti-tumoral action of cannabinoids: involvement of sustained ceramide accumulation and extracellular signal-regulated kinase activation," *Nature Medicine* Mar. 2000; 6(3): 313-319.

Grotenhermen F., "Pharmacokinetics and Pharmacodynamics of Cannabinoids," Clin Pharmacokinet. 2003;42(4):327-60.

Guzmán, Cannabinoids: potential anticancer agents. Nat Rev Cancer. Oct. 2003;3(10):745-55.

Huang et al., ECRG2 inhibits cancer cell migration, invasion and metastasis through the down-regulation of uPA/plasmin activity. Carcinogenesis. Nov. 2007;28(11):2274-81. Epub Jun. 29, 2007.

Hulkower et al., Cell migration and invasion assays as tools for drug discovery. Pharmaceutics. 2011;3:107-24.

Jacobsson, S.O.P. et al., "Inhibition of rat C6 glioma cell proliferation by endogenous and synthetic cannabinoids. Relative involvement of cannabinoid and vanilloid receptors" *J. Pharmacology and Expt. Therapeutics* 2001; 299(3): 951-959.

Killestein et al., Safety, tolerability, and efficacy of orally administered cannabinoids in MS. Neurology. May 14, 2002;58(9):1404-7.

Levy, J.A. et al., "Modulation of the metastatic frequency of a murine mammary adenocarcinoma by a synthetic cannabinoid drug," *Proceedings of the American Association for Cancer Research* 1979; 20: 624.

Nurmikko et al., Sativexsuccessfully treats neuropathic pain characterised by allodynia: a randomised, double-blind, placebo-controlled clinical trial. Pain. Dec. 15, 2007;133(1-3):210-20. Epub Nov. 7, 2007.

Portella, Giuseppe et al., "Inhibitory effects of cannabinoid CB1 receptor stimulation on tumor growth and metastatic spreading: actions on signals involved in angiogenesis and metastasis," *The FASEB Journal: Official Publication of the Federation of American Societies for Experimental Biology*; Sep. 2003; 17(12): 1771-1773.

Strasser et al., Comparison of orally administered cannabis extract and delta-9-tetrahydrocannabinol in treating patients with cancer-related anorexia-cachexia syndrome: a multicenter, phase III, randomized, double-blind, placebo-controlled clinical trial from the Cannabis-In-Cachexia-Study-Group. J Clin Oncol. Jul. 20, 2006;24(21):3394-400.

The United Kingdom Parliament, Select Committee on Science and Technology Ninth Report (1998) at http://www.parliament.the-stationery-office.co.uk/pa/Id199798/Idselect/Idsctech/151/15101.htm.

The United Kingdom Parliament, Select Committee on Science and Technology Second Report (Mar. 14, 2001) at http://www.publications.parliament.uk/pa/Id200001/Idselect/Idsctech/50/5001.htm.

Tucker et al., Effects of cannabinoids on L1210 murine leukemia. 1.Inhibition of DNA synthesis. Res Commun Chem Pathol Pharmacol. Aug. 1977;17(4):703-14.

Velasco, G. et al., "Hypothesis: cannabinoid therapy for the treatment of gliomas?" *Neuropharmacology* Sep. 2004; 47: 315-323.

Gilbert et al., A phase II study of temozolomide in patients with newly diagnosed supratentorial malignant glioma before radiation therapy. Neuro Oncol. Oct. 2002;4(4):261-7.

Robins et al., Phase 2 trial of radiation plus high-dose tamoxifen for glioblastoma multiforme: RTOG protocol BR-0021. Neuro Oncol. Jan. 2006;8(1):47-52.

ANTI-TUMOURAL EFFECTS OF CANNABINOID COMBINATIONS

RELATED APPLICATIONS

This application is a national stage filing under 35 U.S.C. §371 of international application PCT/GB2009/050621, filed Jun. 4, 2009, which was published under PCT Article 21(2) in English.

The present invention relates to the use of a combination of cannabinoids in the manufacture of a medicament for use in the treatment of cancer. In particular the cancer to be treated is a brain tumour, more particularly a glioma, more particularly still a glioblastoma multiforme (GBM) and the preferred cannabinoid combination comprises tetrahydrocannabinol (THC) and cannabidiol (CBD).

BACKGROUND TO THE INVENTION

Cancer a disease in which a group of cells display the traits of uncontrolled growth. This means that the cells grow and divide beyond the levels of normal limits. The cells are also able to invade and destroy surrounding tissues. In addition cancer cells sometimes also metastasize, meaning that they spread to other locations in the body via the blood or lymph.

Most cancers are caused by abnormalities in the genetic material of the cells. These abnormalities may be due to the effects of carcinogens. Other cancer-promoting genetic abnormalities may be randomly acquired through errors in DNA replication, or are inherited, and thus present in all cells from birth.

Genetic abnormalities found in cancer typically affect two general classes of genes. Cancer-promoting oncogenes are often activated in cancer cells, giving those cells new properties, such as hyperactive growth and division, protection against programmed cell death, loss of respect for normal tissue boundaries, and the ability to become established in diverse tissue environments.

Tumour suppressor genes are often inactivated in cancer cells, resulting in the loss of normal functions in those cells, such as accurate DNA replication, control over the cell cycle, orientation and adhesion within tissues, and interaction with protective cells of the immune system.

There are many different types of cancer and the cancer is usually classified according to the type of tissue from which it originated.

Cancer is usually treated by one or more of the following: surgery, chemotherapy, radiation therapy, immunotherapy and monoclonal antibody therapy. The type of therapy depends upon the location and grade of the tumour and the stage of the disease.

Complete removal of the cancer without damage to the rest of the body is the goal of treatment. Sometimes this can be accomplished by surgery, but the propensity of cancers to invade adjacent tissue or to spread to distant sites by microscopic metastasis often limits its effectiveness. The effectiveness of chemotherapy is often limited by toxicity to other tissues in the body. Radiation can also cause damage to normal tissue.

Cancers are known to affect many areas of the body with the most common types of cancers including: cancer of the bile duct, cancer of the bladder, cancer of the bone, cancer of the bowel (including cancer of the colon and cancer of the rectum), cancer of the brain, cancer of the breast, cancer of the neuroendocrine system (commonly known as a carcinoid), cancer of the cervix, cancer of the eye, cancer of the oesophagus, cancer of the head and neck (this group includes carcinomas that start in the cells that form the lining of the mouth, nose, throat, ear or the surface layer covering the tongue), Kaposi's sarcoma, cancer of the kidney, cancer of the larynx, leukaemia, cancer of the liver, cancer of the lung, cancer of the lymph nodes, Hodgkin's lymphoma, non-Hodgkin's lymphoma, melanoma, mesothelioma, myeloma, cancer of the ovary, cancer of the pancreas, cancer of the penis, cancer of the prostate, skin cancer, soft tissue sarcomas, cancer of the spinal cord, cancer of the stomach, testicular cancer, cancer of the thyroid, cancer of the vagina, cancer of the vulva and cancer of the uterus.

A tumour that develops in the brain can destroy or damage brain cells by producing inflammation, compressing other parts of the brain, inducing cerebral oedema (brain swelling) and can cause increases in intracranial pressure (pressure within the skull).

Each year, approximately 4300 people in the UK are diagnosed with a brain tumour. A primary brain tumour is a mass created by the growth or uncontrolled proliferation of cells in the brain. Malignant primary brain tumours are most likely to cause problems by spreading into the normal brain tissue which surrounds them and causing pressure and damage to the surrounding areas of the brain. These tumours rarely spread outside the brain to other parts of the body. However, secondary brain tumours occur when cancer cells from other parts of the body, such as the lung or breast spread to the brain.

Surgery is the treatment option of choice for many brain tumours. Some may be completely excised, but those that are deep or that infiltrate brain tissue may be debulked rather than removed.

Radiation therapy and chemotherapy may be recommended depending on the type of tumour involved.

Glioma cell tumours can often be lethal. The characteristic diffuse infiltrative tumour growth of gliomas often makes the surgical removal of them impossible and this profoundly complicates the clinical management of these patients.

Glioblastoma multiforme (GBM) is the most common and most aggressive type of primary brain tumour and accounts for 52% of all primary brain tumour cases and 20% of all intracranial tumours.

Different approaches are being researched in order to improve the mortality rate of patients diagnosed with a glioma. These include therapies that target the glioma cells but leave normal cells unharmed, methods that limit the spread of the cancer cells and treatments that block the tumours life-sustaining molecules.

One such area of research involves the use of cannabinoids as anti-tumoural agents.

Cannabinoids are the active constituents of *cannabis* plants and they have been found to demonstrate numerous pharmacological properties.

For example EP1177790 (Guzman et al.) describes the treatment of cerebral tumours by the administration of a natural or synthetic cannabinoid, specifically THC. It is claimed that activation of specific receptors leads to selective death of the transformed cells.

Recently the cannabinoid CBD has been shown to possess anti-tumoural properties (Massi et al. 2004). The work described by this paper describes anti-proliferative effects both in-vitro using U87 and U373 human glioma cell lines and in-vivo using U87 human glioma cells subcutaneously implanted to nude mice.

Malignant gliomas are highly infiltrative and proliferative tumours, which follow a characteristic pattern of growth. Glioma cells invade the adjacent normal brain structures and surrounding large blood vessels.

In addition the applicant's earlier patent EP1802274 describes the use of the cannabinoid CBD to impede the progress of cancer cells migrating from their primary tumour location to a secondary site.

Furthermore, Medical hypothesis (2006) vol 66, pages 234-246 discusses the physiological and clinical effects of THC and CBD and presents a rationale for their combination. Under "neoplastic disease" (page 242) it is acknowledged that THC has cytotoxic benefits and that CBD has also proven cytostatic/cytotoxic. It is suggested, given the analgesic effects of the CBD:THC combination in cancer treatment, the side benefit of THC and CBD in chemotherapy induced nausea, and these primary effects on tumor growth and spread that there is a strong rational for additional clinical trials. However, the generality of this teaching could not have predicted the benefits that could be achieve in combination in what would otherwise have been considered sub-optimal (or ineffective amounts) for the compounds alone.

SUMMARY OF INVENTION

According to the present invention there is provided the use of a combination of cannabinoids in the manufacture of a medicament for use in the treatment of cancer.

Preferably the cannabinoids comprise at least tetrahydrocannabinol (THC) and cannabidiol (CBD).

Preferably the THC and CBD are in a ratio of from between 20:1 to 1:20 (THC:CBD).

More preferably the THC and CBD are in a ratio of from between 5:1 to 1:5 (THC:CBD).

More preferably still, the THC and CBD are in a ratio of between 2:1 to 1:2, more preferably still, approximately 1:1.

Each cannabinoid is provided in a therapeutically effect amount. Dose ranges for the THC and CBD may be determined by reference to the cannabinoid content which is preferably in the range of between 5 and 100 mg of the total cannabinoids.

The cancer to be treated may be a brain tumour.

Brain tumours are usually classified according to the location of the tumour and the type of cell that the cancer has developed from.

For example different types of brain tumour include: acoustic neuroma, astrocytoma, CNS lymphoma, ependymoma, haemangioblastoma, medulloblastoma, meningioma, glioma, mixed glioma, oligodendroglioma, pineal region tumours and pituitary tumours.

Gliomas are tumours of the glial cells; these cells support and protect nerve cells in the brain. Gliomas comprise nearly half of all primary brain tumours and a fifth of all primary spinal cord tumours.

The cannabinoid combination of the invention is particularly useful where the brain tumour is a glioma tumour, more particularly glioblastoma multiforme (GBM).

The one or more cannabinoids may be present as plant extracts, as pure compounds, or a combination of the two.

A plant extract is defined as an extract from a plant material as described by the Guidance for Industry Botanical Drug Products Draft Guidance, August 2000, US Department of Health and Human Services, Food and Drug Administration Centre for Drug Evaluation and Research.

Plant material is defined as a plant or plant part (e.g. bark, wood, leaves, stems, roots, flowers, fruits, seeds, berries or parts thereof) as well as exudates.

More preferably the plant extract is in the form of a botanical drug substance.

Botanical drug substances which are derived from *cannabis* plants include primary extracts prepared by such processes as for example, maceration, percolation, extraction with solvents such as C1 to C5 alcohols (e.g. ethanol), Norflurane (HFA134a), HFA227, liquid carbon dioxide under pressure and extraction using a hot gas. A primary extract may be further purified by supercritical or subcritical extraction, vaporisation and chromatography. When solvents such as those listed above are used the resultant extract may contain non-specific lipid-soluble material. This can be removed by a variety of processes including winterisation, which involves chilling to $-20°$ C. followed by filtration to remove waxy ballast, extraction with liquid carbon dioxide and by distillation.

Botanical drug substances are formulated into Botanical Drug Products which are defined in the Guidance for Industry Botanical Drug Products Draft Guidance, August 2000, US Department of Health and Human Services, Food and Drug Administration Centre for Drug Evaluation and Research as: "A botanical product that is intended for use as a drug; a drug product that is prepared from a botanical drug substance."

The one or more cannabinoids may be administered separately, sequentially or simultaneously to one another.

Certain aspects of this invention are further described, by way of example only, with reference to the accompanying drawings in which.

SPECIFIC DESCRIPTION

The following examples describe experiments undertaken to ascertain the effect of combinations of cannabinoids as anti-tumoural agents.

Example 1

The Effect of THC and CBD at Inhibiting Cancer Cell Growth In Vitro

Tetrahydrocannabinol (THC) and cannabidiol (CBD) in the form of *cannabis* plant extracts were dissolved in ethanol to a concentration of 100 mM this was stored at $-20°$ C. until required.

Before use the *cannabis* plant extracts were further diluted to the desired concentration, ensuring that the concentration of ethanol was below 0.001%.

U87 human glioma cells were used throughout this experiment. The cells were maintained at $37°$ C. in a humidified atmosphere with 5% $CO_2$ and 95% air.

Cells were cultured in a 75 $cm^2$ culture flask in Dulbecco's Modified Eagle Medium (DMEM), which had been supplemented with 4 mM L-glutamine, 100 units/ml penicillin, 100 mg/ml streptomycin, 1% sodium pyruvate, 1% non-essential amino acids and 10% heat-inactivated fetal bovine serum.

The viability of the human U87 MG astrocytoma cells were examined at various cannabinoid concentrations. The THC and CBD extracts were compared against pure THC and CBD.

Results:

TABLE 1

Cell viability of human U87 MG astrocytoma cells in culture

| | IC50 μM (pure cannabinoids) | IC50 μM (cannabis plant extract) | IC50 μM (equivalent of pure in cannabis plant extract) |
|---|---|---|---|
| THC | 0.37 | 0.64 | 0.43 |
| CBD | 0.47 | 0.72 | 0.47 |

As can be seen from Table 1 above the THC and CBD extracts compare very favourably in activity to their corresponding pure compounds, when the amount of cannabinoid in the extract is adjusted to an equivalent amount of pure compound.

This shows that THC and CBD and their extracts are effective in inhibiting glioma cell growth.

Example 2

The Effect of a Combination of THC and CBD Extracts at Inhibiting Cancer Cell Growth In Vitro This experiment tested whether a combination of THC and CBD extracts were as effective at inhibiting cell growth as the extracts alone.

The methods used were as described in Example 1 above.

Figure 1:
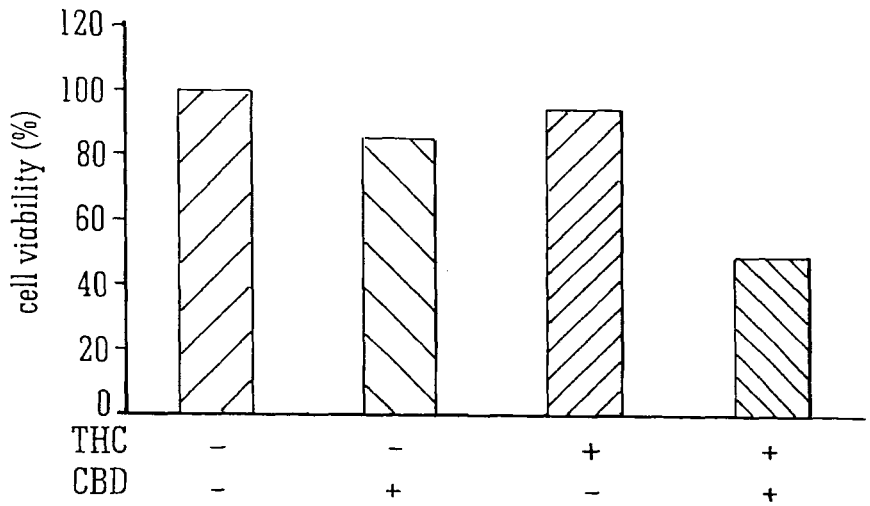
FIG. 1 is a bar chart showing the cell viability of human U87 MG astrocytoma cells after treatment with THC, CBD or a combination of THC and CBD in comparison to a control.

Results:

FIG. 1 details a bar chart describing the cell viability of human U87 MG astrocytoma cells versus the THC and CBD extracts alone and in combination with one another.

As can be seen when the THC and CBD are used in combination the cell viability is significantly reduced in comparison to the cell viability after treatment with either THC or CBD alone.

This data suggests that the cannabinoids THC and CBD would be more effective in the treatment of tumours when used in combination.

Example 3

The Effect of a Combination of THC and CBD at Inhibiting Cancer Cell Growth In Vivo This experiment tested whether the combination of THC and CBD extracts were also effective in vivo.

Human U87 MG astrocytoma cells were xenografted to nude mice and the test compounds were injected peritumourally at a concentration of 15 mg/kg per day.

Results:

TABLE 2

Tumour volume relative to zero time following 15 days of treatment

| | Tumour volume |
|---|---|
| Vehicle | 9.2 ± 0.6 |
| Pure THC | 5.1 ± 0.4 |
| THC extract | 6.6 ± 0.3 |
| THC:CBD (1:1) extract | 4.8 ± 0.3 |

As can be observed in Table 2 above the tumour volume after treatment with the 1:1 combination of THC and CBD extracts is significantly superior to the treatment with either the pure THC or the THC extract alone.

This data suggests that the cannabinoids THC and CBD would be more effective in the treatment of tumours when used in combination.

Example 4

Effect of Cannabinoid Concentration on Cell Viability in Two Different Cell Lines The action of THC, CBD, and a 1:1 ratio mix of THC and CBD were studied at different concentrations on two cell lines: U87MG and T98G. The cell viability data is illustrated in FIGS. 2a and 2b.

Figure 2A:
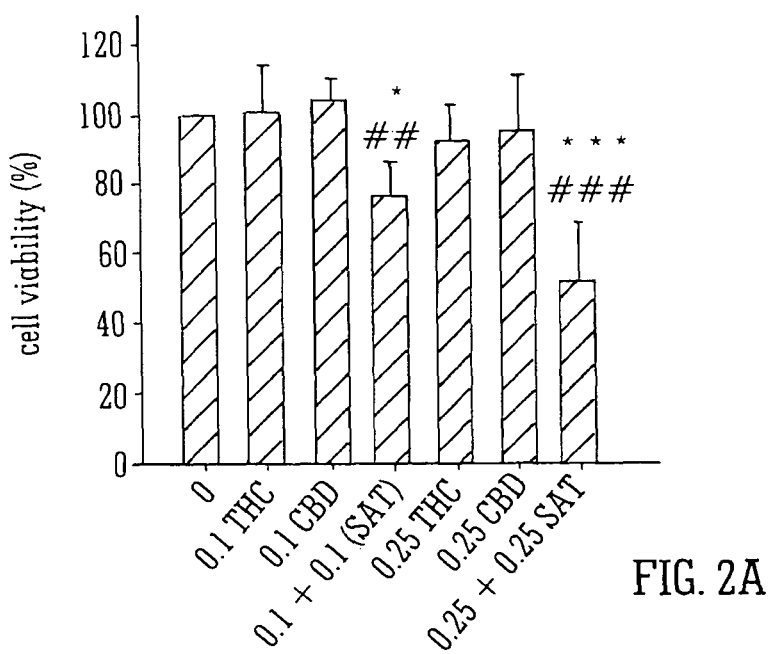
FIGS. 2a and 2b are bar charts showing in vivo cell viability data at different concentrations on two cell lines, U87MG (FIG. 2a) and T98G (FIG. 2b)

Referring to FIG. 2a it will be seen that ineffective/sub-optimal doses of THC and CBD at 0.1 ug/ml and 0.25 ug/ml (greater than 90% cell viability) gave way to a statistically significant decrease in cell viability in combination (SAT), which data showed a dose dependant relationship with increased concentration (greater cyto-toxicity at 0.25 ug/ml).

Figure 2B:
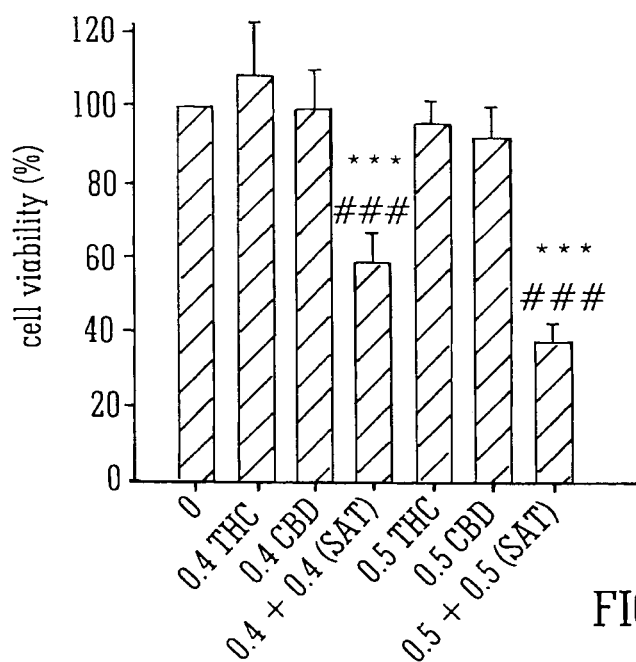

Similar results were obtained with cell line T98G, (an alternative human glioma cell line) as is shown in FIG. 2b.

Example 5

Investigation of Mechanism of Action

THC is known to induce cell death using a signalling route involving the gene ATG1 and pan-caspase. The results of an investigation looking at S6 phosphorylation, LC3 lipidation and the effect of an ATG1 and a pan-caspase inhibitor are shown in FIGS. 3a, 3b and 3c respectively.

Figure 3A:
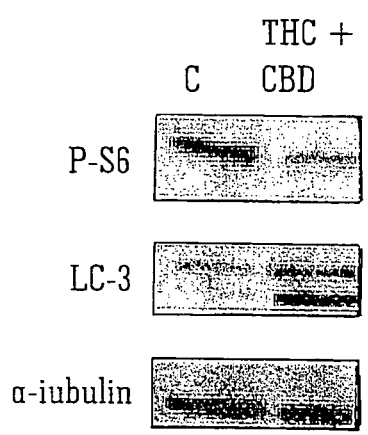
FIGS. 3a, 3b and 3c provide data suggestive of the mechanism of action of the combination for U87MG cells.

It can be seen from FIG. 3a that the THC:CBD combination (compare to control C):

Inhibits mTORC1 activity (as determined by the levels of S6 phosphorylation); and Promotes accumulation of the lipidated form LC3 (a hall mark of autophagy).

Figure 3B:
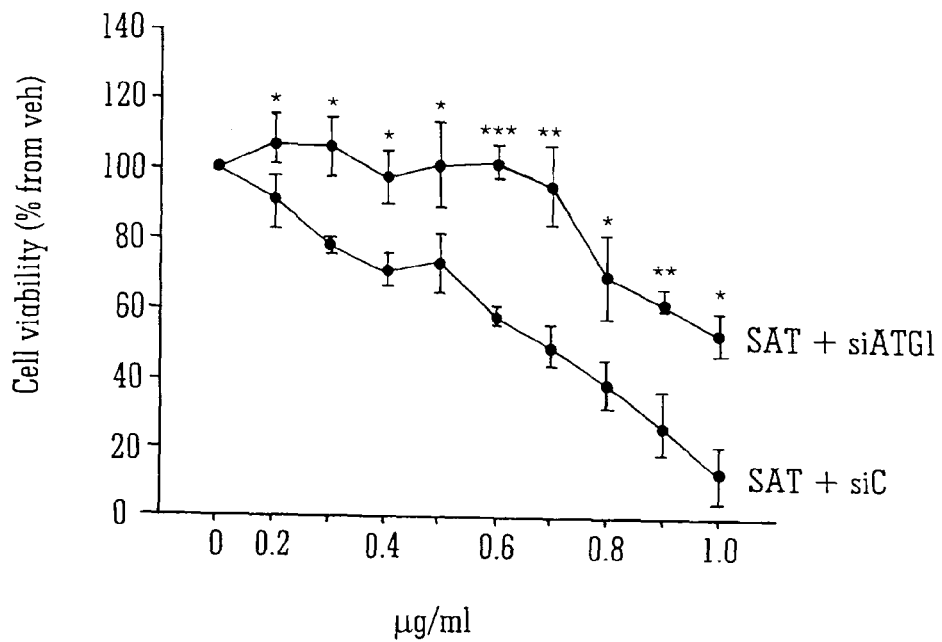
Figure 3C:
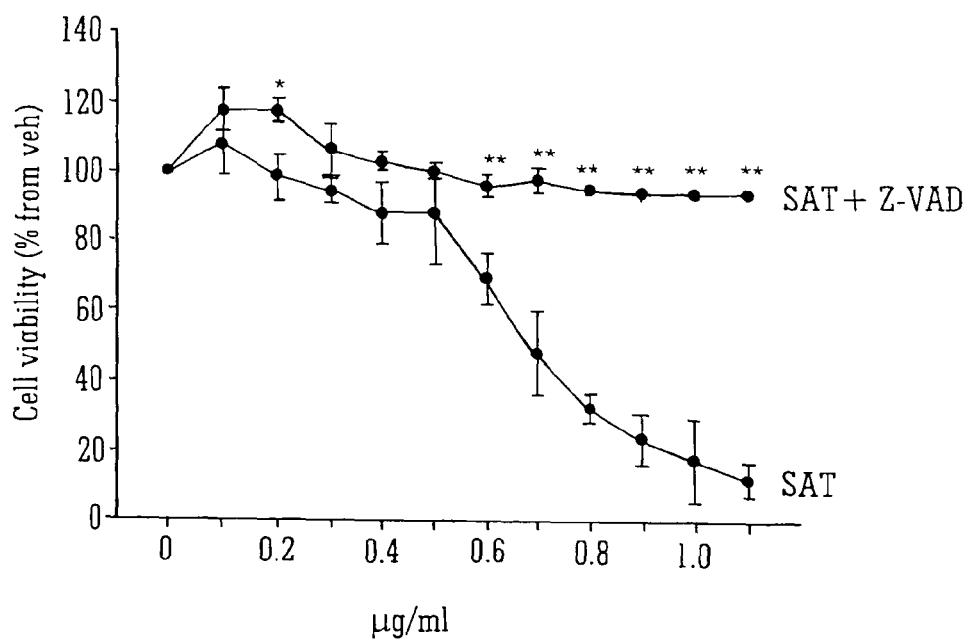

FIG. 3b shows that silencing the essential autophagy gene ATG1, with a selective (siATG10) siRNA inhibitor reduces induced cell death compared to cells transfected with a control siC.

Finally, FIG. 3c shows that cells treated with the pancapase inhibitor Z-VAD also prevent induced cell death.

The invention claimed is:

1. A method for treating glioblastoma multiforme in a human in need thereof consisting essentially of administering to said human therapeutically effective amounts of cannabidiol (CBD) and tetrahydrocannabinol (THC) in combination as pure cannabinoids wherein the cannabinoids are in a ratio of from 1:1 to 1:20 (THC:CBD).

2. The method of claim 1, wherein the treatment of the glioblastoma multiforme in a human in need thereof is to reduce cell viability, reduce cell growth or reduce tumour volume.

3. The method of claim 1, wherein the THC and CBD are administered separately, sequentially or simultaneously to said human.

\* \* \* \* \*

UNITED STATES PATENT AND TRADEMARK OFFICE
CERTIFICATE OF CORRECTION

| | | |
|---|---|---|
| PATENT NO. | : 8,632,825 B2 | Page 1 of 1 |
| APPLICATION NO. | : 12/996124 | |
| DATED | : January 21, 2014 | |
| INVENTOR(S) | : Velasco Diez et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 43 days.

Signed and Sealed this
Second Day of June, 2015

Michelle K. Lee
*Director of the United States Patent and Trademark Office*